(12) United States Patent
Biedermann

(10) Patent No.: US 10,716,607 B2
(45) Date of Patent: Jul. 21, 2020

(54) CABLE RETAINING INSERT AND BONE PLATE ASSEMBLY WITH SUCH A CABLE RETAINING INSERT

(71) Applicant: Biedermann Technologies GmbH & Co. KG, Donaueschingen (DE)

(72) Inventor: Markku Biedermann, Miami, FL (US)

(73) Assignee: Biedermann Technologies GmbH & Co. KG, Donaueschingen (DE)

(*) Notice: Subject to any disclaimer, the term of this patent is extended or adjusted under 35 U.S.C. 154(b) by 161 days.

(21) Appl. No.: 15/903,519

(22) Filed: Feb. 23, 2018

(65) Prior Publication Data

US 2018/0256228 A1    Sep. 13, 2018

Related U.S. Application Data

(60) Provisional application No. 62/470,740, filed on Mar. 13, 2017.

(51) Int. Cl.
| | |
|---|---|
| *A61B 17/56* | (2006.01) |
| *A61B 17/58* | (2006.01) |
| *A61B 17/82* | (2006.01) |
| *A61F 2/30* | (2006.01) |
| *A61B 17/80* | (2006.01) |
| *A61B 17/84* | (2006.01) |
| *A61B 17/86* | (2006.01) |

(52) U.S. Cl.
CPC .......... *A61B 17/82* (2013.01); *A61B 17/8014* (2013.01); *A61B 17/8042* (2013.01); *A61B 17/8057* (2013.01); *A61B 17/842* (2013.01); *A61B 17/8605* (2013.01)

(58) Field of Classification Search
USPC .................................. 606/269, 232, 220, 74
See application file for complete search history.

(56) References Cited

U.S. PATENT DOCUMENTS

| | | | |
|---|---|---|---|
| 5,190,545 A | 3/1993 | Corsi et al. | |
| 8,343,155 B2 | 1/2013 | Fisher et al. | |
| 8,808,335 B2 | 8/2014 | Biedermann | |
| 2009/0287215 A1* | 11/2009 | Fisher ................ | A61B 17/80 606/71 |
| 2014/0243907 A1 | 8/2014 | Cavallazzi et al. | |
| 2015/0289914 A1 | 10/2015 | Forderer et al. | |

FOREIGN PATENT DOCUMENTS

| | | |
|---|---|---|
| EP | 0791338 A2 | 8/1997 |
| EP | 0791338 B1 | 8/2003 |

* cited by examiner

*Primary Examiner* — Sameh R Boles
(74) *Attorney, Agent, or Firm* — Gordon & Jacobson, P.C.

(57) ABSTRACT

A cable retaining insert is configured to be used with a plate member of a bone plate assembly. The cable retaining insert includes a top side and an opposite bottom side, a first portion and a second portion. The first portion is adjacent to the bottom side and includes an engagement structure configured to engage a corresponding engagement structure in the plate member. The second portion is adjacent to the top side and includes at least one cable retaining aperture configured to retain a cable to the plate member. The first portion of the cable retaining insert has a recess at the bottom side for accommodating at least a portion of a head of a bone anchor. Furthermore, a bone plate assembly including a plate member and such a cable retaining insert is provided.

8 Claims, 5 Drawing Sheets

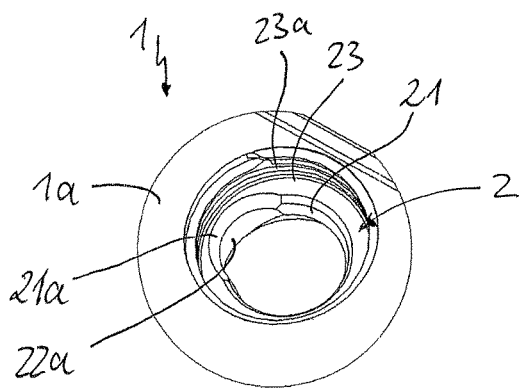
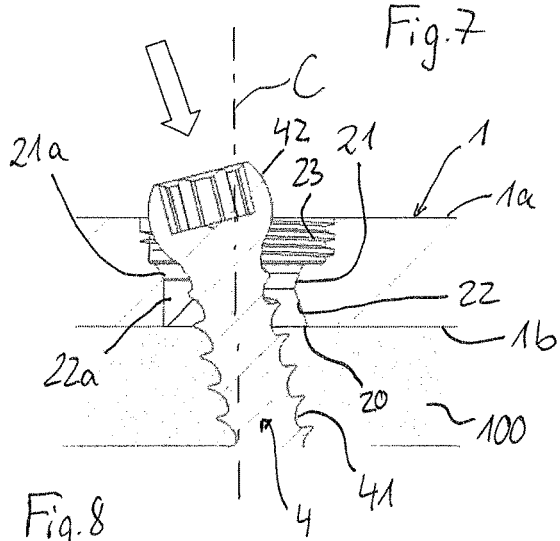
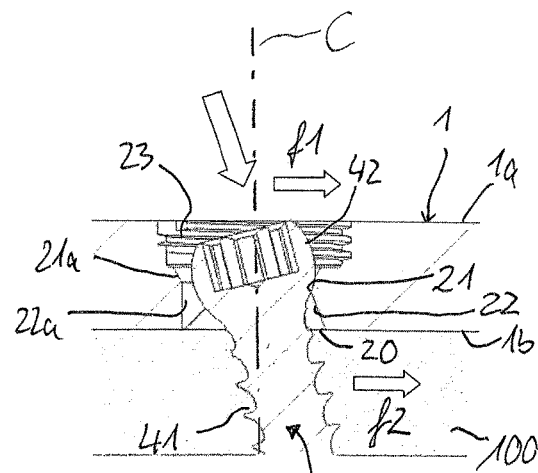
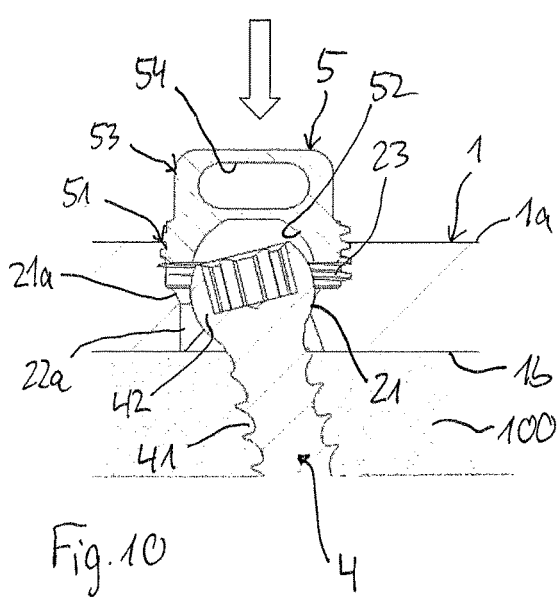
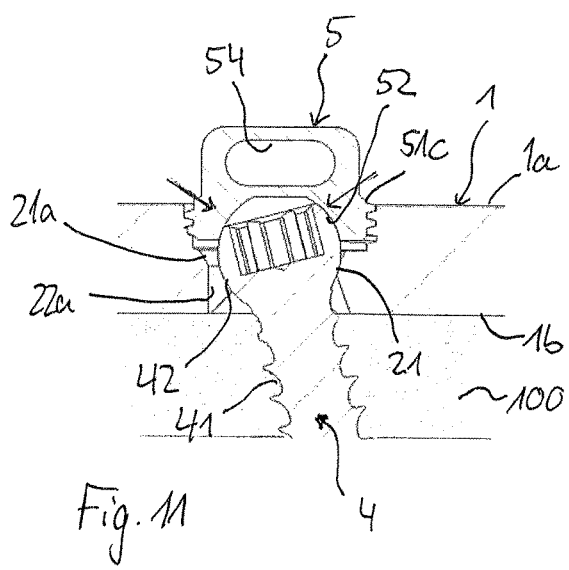

ND BONE
CABLE RETAINING INSERT AND BONE PLATE ASSEMBLY WITH SUCH A CABLE RETAINING INSERT

CROSS-REFERENCE TO RELATED APPLICATIONS

This application claims benefit to U.S. Provisional Application Ser. No. 62/470,740, filed Mar. 13, 2017, which is hereby incorporated by reference herein in its entirety.

BACKGROUND OF THE INVENTION

1. Field of the Invention

The present invention relates to a cable retaining insert and to a bone plate assembly with such a cable retaining insert. The cable retaining insert and the bone plate assembly are suitable for use in methods of fracture fixation using cerclage wiring techniques.

2. State of the Art

U.S. Pat. No. 5,190,545 describes a bone fracture stabilization apparatus including a cable positioning insert for a bone plate of the type having a series of apertures therein for receiving bone screws for attaching the bone plate to the bone. The cable positioning insert has a body shaped for at least partial insertion into at least one of the apertures of the bone plate.

U.S. Pat. No. 8,343,155 B2 describes an apparatus such as a cable button for use with a bone plate, the cable button including cable button threads, a plurality of cable button apertures, a hex socket, and a hex opening. The cable button is secured, such as by threading, to the bone plate by bone plate apertures. A cerclage wire is secured to the bone plate by use of the cable buttons.

U.S. Pat. No. 8,808,335 B2 describes a locking element configured to be used with a bone plate assembly. The position of the bone anchor relative to the plate has an angular stability due to the locking element.

SUMMARY OF THE INVENTION

It is the object of the invention to provide a cable retaining insert and a bone plate assembly with such a cable retaining insert that is simple to use and increases the variety of applications of the bone plate.

The cable retaining insert can be used in a hole of a bone plate without the necessity of providing a bone anchor in the hole. Alternatively, the cable retaining insert can be inserted into a hole of a bone plate when a bone anchor is already placed in the hole to anchor the bone plate to the bone. In this case, the cable retaining insert may be used simultaneously for securing the head of the bone anchor in the hole and for guiding a cable or wire through the insert for cerclage wiring. The cable retaining insert provides angular stability of the bone anchor relative to the bone plate in the same manner as a locking element. Moreover, the bone anchor is secured against pull-out.

With the cable retaining insert provided in a hole of the bone plate, the bone plate has a low profile as only an eyelet of the cable retaining insert protrudes from the surface.

One or more holes of the bone plate can have a recess forming a ramp that permits the head of the bone anchor to be pressed into the seat of the hole when the bone anchor is screwed into the bone. Thereby, the bone fragments of the fracture may be compressed against each other which improves the fixation and the healing. With the additional fixation using a cable for cerclage wiring the stability of the fixation can be further improved.

BRIEF DESCRIPTION OF THE DRAWINGS

FIG. 7 shows an enlarged perspective view from above of a hole of the bone plate of the bone plate assembly of FIGS. 1 and 2.

FIGS. 8 to 11 show cross-sectional views of steps of inserting a bone anchor into a hole of the bone plate and using the cable retaining insert of FIGS. 1 to 6.

DETAILED DESCRIPTION OF THE PREFERRED EMBODIMENTS

Figure 1:
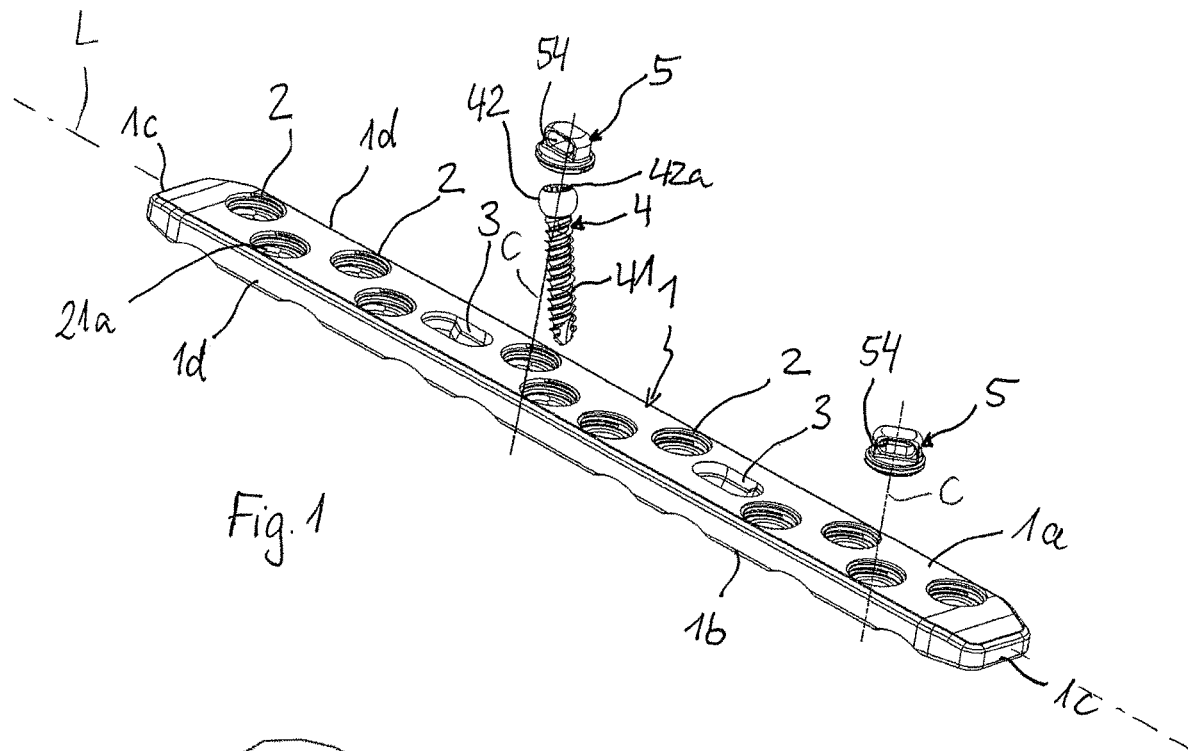
FIG. 1 shows a perspective view of a bone plate assembly according to a first embodiment.

FIG. 1 is a first embodiment of the bone plate assembly which will now be described with reference to FIGS. 1 to 6. The bone plate assembly includes a plate member 1 which is in this embodiment a substantially rectangular body with a top side 1a, a bottom side 1b, short sides 1c and long sides 1d and a longitudinal axis L defining a longitudinal direction. A plurality of holes 2 that form a first type of holes extend through the plate member 1 from the top side 1a to the bottom side 1b. Holes 3 according to a second type of holes may be provided in between the first type of holes 2.

The bone plate assembly further comprises at least one bone anchor 4 that is configured to be inserted into the first holes 2 and may be also insertable into the second holes 3. The bone anchor 4 may be in the form of a bone screw having a threaded shank 41 and a head 42. The head 42 has a spherical outer surface portion and optionally a recess 42a at the free end of the head 42 opposite to the shank for engagement with a screw driver.

The bone plate assembly further includes at least one cable retaining insert 5 that is configured to be inserted into one of the holes 2.

Figure 2:
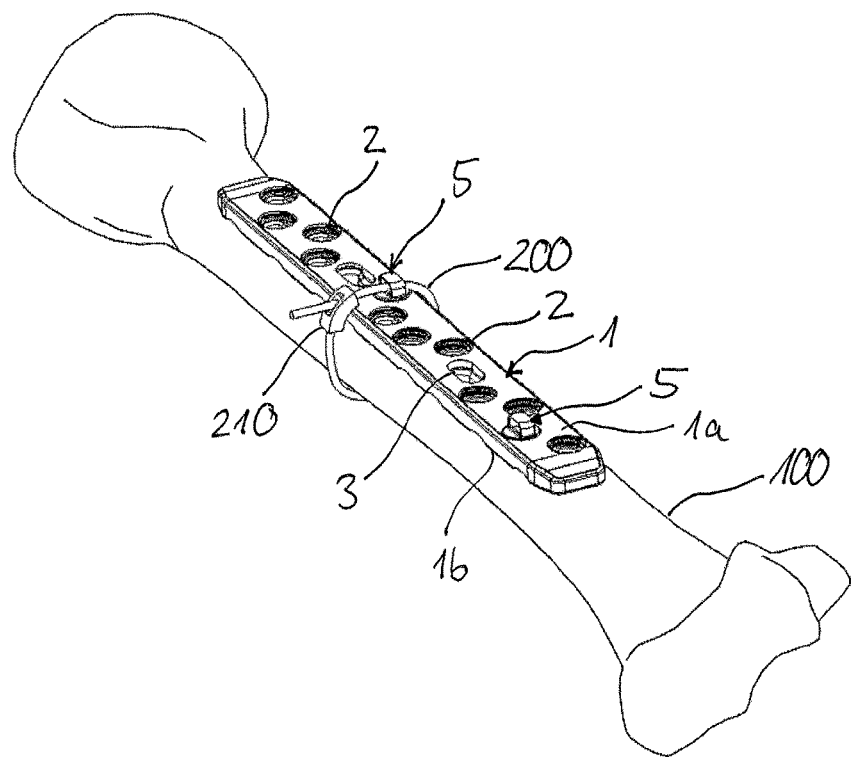
FIG. 2 shows a perspective view of the bone plate assembly of FIG. 1 in an assembled state used for fixation of a fracture of a long bone with a cerclage wiring technique.
Figure 3:
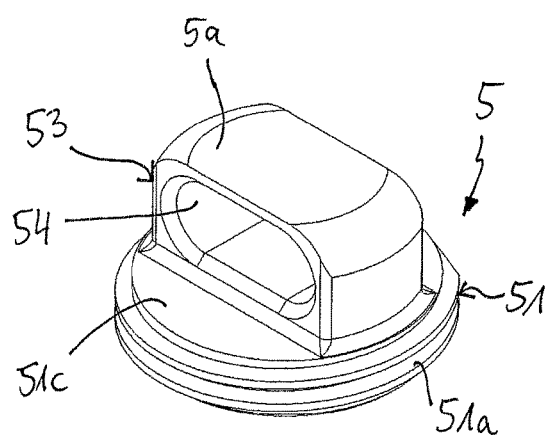
FIG. 3 shows a perspective view from the top of a cable retaining insert according to a first embodiment.
Figure 4:
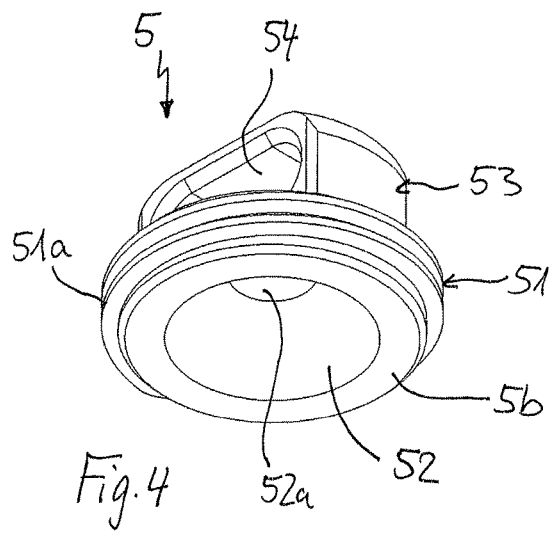
FIG. 4 shows a perspective view from the bottom of the cable retaining insert of FIG. 3.
Figure 5:
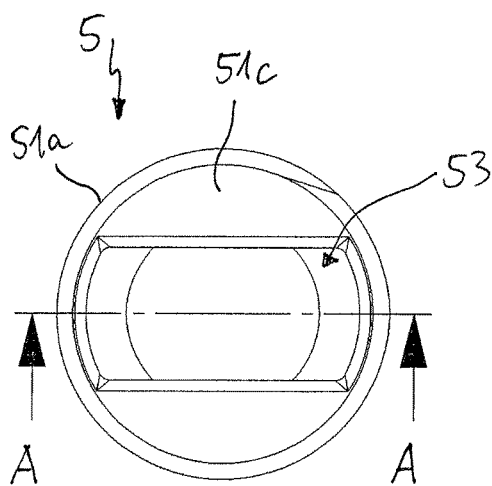
FIG. 5 shows a top view of the cable retaining insert of FIGS. 3 and 4.
Figure 6:
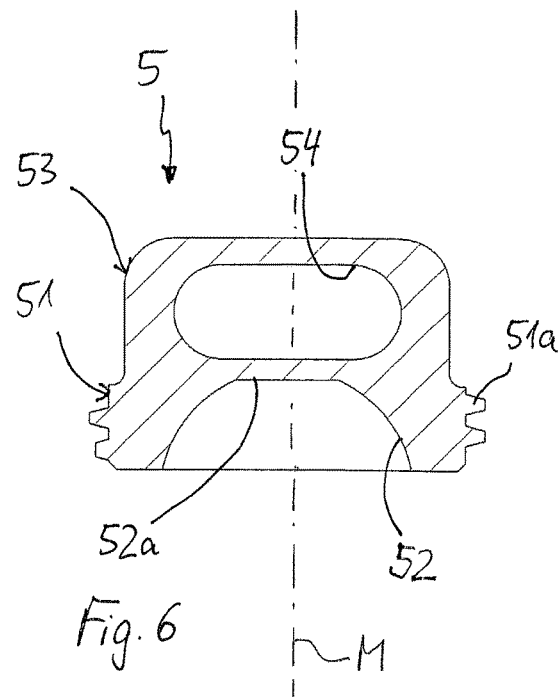
FIG. 6 shows a cross-sectional view of the cable retaining insert of FIGS. 3 to 5, the cross-section taken along line A-A in FIG. 5.

The bone plate assembly may be used to stabilize and/or immobilize a bone, for example in the case of a fracture. As depicted in FIG. 2, a long bone 100 is immobilized using the plate member 1 that contacts the bone with at least a portion of its bottom side 1b and a cable 200 that is pulled through the cable retaining insert 5 and wound around the long bone, tightened and fixed with a fixation device 210, for example, using a clamping mechanism. The term "cable" includes any longitudinal and at least partially flexible element that is configured to be used for a cerclage wiring technique. The cable 200 can be elastic. It can be made of a plastic material, of a metal wire, of tissue or any other suitable material.

Referring now first to FIGS. 1, 7 and 8 to 11, the shape of the hole 2 will be described. The hole 2 comprises an opening 20 at the bottom side 1b, the inner diameter of which is greater than an outer diameter of the threaded shank 41 of the bone anchor 4, so that the threaded shank 41 can pass therethrough. The diameter is, however, smaller than the largest outer diameter of the head 42, so that the head 42 is not able to pass through the lower opening 20. Between the top side 1a and the bottom side 1b a seat portion 21 is formed that forms a socket for accommodating the head 42 in various angular positions of the shank 41 relative to the plate member 1. In the embodiment shown, the seat portion 21 is spherically-shaped with a radius that matches the radius of the spherically-shaped portion of the head 42. The seat portion 21 allows to insert the bone anchor 4 at any desired angle. Between the seat portion 21 and the lower opening 20 a conically-shaped passage 22 is formed that narrows from the opening 20 towards the seat portion 21. Between the seat portion 21 and the top side 1a a cylindrical bore 23 defining a central axis C of the hole 2 and having an internal thread 23a in at least a portion thereof is provided. The inner diameter of the bore 23 is larger than the inner diameter of the seat portion 21 and larger than the outer diameter of the head 42. By means of this, access to the head 42 with a screw driver is possible even at large insertion angles.

At one side from the central axis C of the hole 2 a ramp is provided that permits the head 42 to be pressed into the seat portion 21 when the anchor is screwed into the bone. The ramp comprises a recess 21a with an inclined wall or a countersink slightly above the seat portion 21 in a direction towards the top side 1a of the plate member 1. The recess 21a extends around a portion of the seat 21 in a circumferential direction and a center of the recess 21a is slightly offset from the central axis C so that when the head 42 touches the recess 21a during insertion the head 42 experiences a force which presses the head 42 laterally and downwards into the seat portion 21. A further recess 22a is provided below the recess 21a that enlarges the conical passage 22 to permit a portion of the head 42 to extend therein when the bone anchor is fully inserted (as depicted, for example, in FIGS. 9 to 11).

The holes 2 are arranged such and oriented with their respective recesses 21a, 22a, i.e. with their ramp, such that in one group of holes 2 the ramp is located towards one of the short sides 1c and in another group of holes 2 the ramp is located towards the other short side 1c of the plate member 1. For example, at least one hole 2 with a ramp located towards one short side 1c may be located at the left side of a middle of the plate member 1 in the longitudinal direction and at least one other hole 2 with a ramp located towards the other short side 1c may be located at the right side from the middle of the plate member 1. However, the location of the holes 2 is not restricted thereto. By means of this, using bone anchors in holes 2 with different orientation of the ramp can be used for compressing the bone fragments together that are bridged with the plate member 1.

The holes 3 of the second type may be elongate holes that permit the bone anchor to be placed at various longitudinal positions with respect to the plate member 1. The holes 3 of the second type may also have a seat and a ramp as described above.

The number and arrangement of holes 2 of the first type and holes 3 of the second type can vary according to the size and shape of the plate member 1. The plate member 1 may have only at least one hole 2 or a plurality of holes 2 and optionally one or more holes 3. The second type of holes 3 may also be omitted.

The cable retaining insert 5 will now be described with reference to FIGS. 3 to 6. The cable retaining insert 5 comprises a top side 5a and an opposite bottom side 5b and a first portion 51 adjacent to the bottom side 5b which is substantially cylindrical and comprises in at least a portion thereof an external thread 51a that is configured to cooperate with the internal thread 23a of the cylindrical recess 23 of the hole 2 of the plate member 1. By the thread axis a central axis M of the insert 5 is defined. The height of the first portion 51 corresponds substantially to the depth of the bore 23, so that as shown for example in FIG. 11, when the cable retaining insert 5 is screwed into the bore 23, an upper side 51c of the first portion 51 is substantially flush with the top side 1a of the plate member 1. As depicted in particular in FIGS. 4 and 6, the cable retaining insert 5 comprises a recess 52 at the bottom side 5b which has in the first embodiment a spherically-shaped portion and fits to the spherically-shaped portion of the head 42. A depth of the recess 52 can be equal to or larger than the radius of the spherical portion of the head 42. With the recess 52 contacting the head 42, the pressure exerted by the cable retaining insert 5 onto the head 42 may be smoothly distributed onto the head 42. The recess 52 may have a substantially flat bottom 52a that forms a flat top when the insert 5 is placed onto the head 42.

The cable retaining insert 5 further includes a second portion 53 adjacent to the top side 5a that has a shape configured to retain a cable. The second portion 53 may be formed in an eyelet-like manner with a closed loop. It comprises at least one aperture 54 for passing a cable 200 therethrough. More in detail, the second portion 53 is formed like a substantially cylindrical projection that projects from the first portion 51 and from which two opposite sections have been cut away so that a width of the second portion 53 in one direction is the same or slightly smaller than a width of the first portion 51 and a width in a direction perpendicular thereto is substantially smaller than a width of the first portion 51. The aperture 54 thus has an elongate cross-section wherein the long sides of the elongate aperture 54 extend in a direction perpendicular to the thread axis. This renders the cable retaining insert 5 compact. Furthermore, the elongate aperture 54 facilitates passing through the cable 200.

The dimensions of the first portion 51 of the cable retaining insert 5, of the cylindrical bore 23 and the cooperating threads 51a, 23a may be such that when the cable retaining insert 5 has been screwed into the cylindrical recess 23 of the hole 2 of the plate member 1 and tightened, the long sides of the elongate aperture 54 extend substantially parallel to the long sides 1b of the plate member 1. Alternatively, a marking may be provided to facilitate the orientation of the elongate aperture 54 such that the cable 200 extends, when passing through the aperture 54, substantially perpendicular to the longitudinal direction of plate member 1 and therefore also substantially perpendicular to the axis of, for example, a long bone.

The plate member 1, the bone anchor 4 and the cable retaining insert 5 may be made of bio-compatible materials, for example, of titanium or stainless steel, of a bio-compatible alloy, such as a NiTi-alloy, for example, Nitinol, of magnesium or magnesium alloys or from a bio-compatible plastic material, such as, for example, polyetheretherketone (PEEK) or poly-1-lactide acid (PLLA). The parts can be made of the same or of different materials.

Referring now to FIGS. 8 to 11, steps of using the bone plate assembly with the cable retaining insert 5 will be described. As shown in FIG. 8, the plate member 1 is applied to the bone 100 such that the bottom side 1b faces a surface of the bone 100. Then, the bone anchor 4 passes with the threaded shank 41 through the hole 2 and is screwed into the bone 100. The bone anchor 4 may be screwed into the bone 100 at an angle relative to the central axis C of the hole 1. As soon as the head 42 touches the ramp provided by the recess 21a the ramp causes the head 42 to be pressed laterally downward until the head 42 is seated in the seat portion 21. This results in a compression force exerted onto the bone part in which the shank 41 is screwed in relative to a neighboring bone part. FIG. 9 illustrates the inserted state of the bone anchor 4 with the arrow f1 schematically shows the force acting onto the head 42 and the arrow f2 schematically shows the force acting onto the bone 100.

As shown in FIG. 10, after the head 42 is seated in the seat portion 21, the cable retaining insert 5 is screwed with its first portion 51 into the threaded bore 23 of the hole 2. Next, as depicted in FIG. 11, the cable retaining insert is tightened until the inner surface of the recess 52 presses onto the head 42 as indicated by the arrows. Thereby, the position of the bone anchor 4 is locked. The cable retaining insert 5 also prevents pull-out of the bone anchor 4.

In use, usually at least two bone anchors 4 are used to fix the plate member 1 to the bone 100. One bone anchor may be placed in a hole 2 on the left side of the middle of the plate member 1 and another bone anchor may be placed into a hole 2 on the right side of the middle of the plate member 1 in the longitudinal direction. Due to the opposite ramps, the resulting forces onto the bone press the two bone fragments together. When the cable retaining inserts 5 are inserted into the holes 2 and tightened, a cable (not shown) may be guided through each of the apertures 54 of the cable retaining inserts 5, wound around the bone fragments and tightened. As a result, thereof a safe and strong fixation is achieved.

Figure 12:
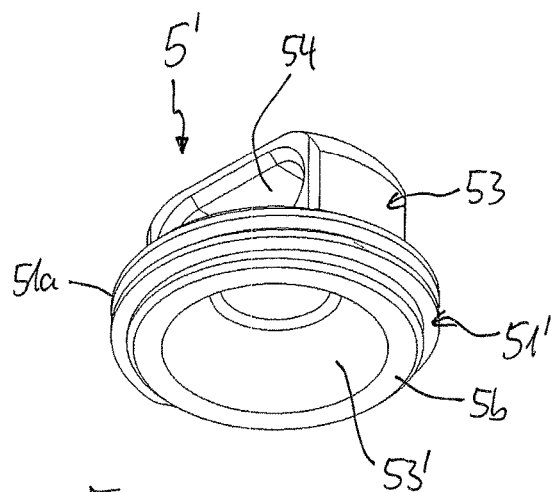
FIG. 12 shows a perspective view from the bottom of a cable retaining insert according to a second embodiment.
Figure 13:
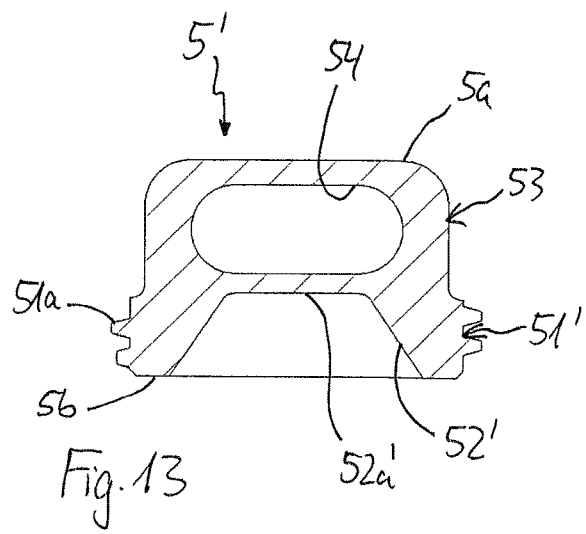
FIG. 13 shows a cross-sectional view of the cable retaining insert of FIG. 12.
Figure 14:
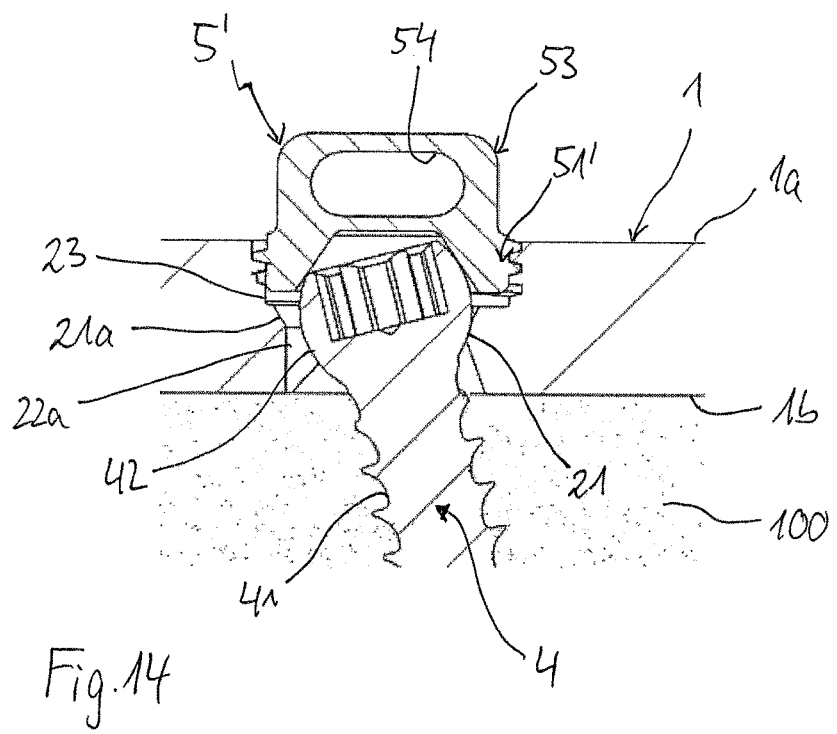
FIG. 14 shows a cross-sectional view of a portion of a bone plate assembly with the cable retaining insert of FIGS. 12 and 13.

A second embodiment of the bone plate assembly will be described with reference to FIGS. 12 to 14. The bone plate assembly differs only in the shape of the cable retaining insert. The cable retaining insert 5' differs from the cable retaining insert 5 of the previous embodiment in the shape of the recess at the bottom side 5b. All other parts and portions are the same as for the first embodiment and the description thereof will not be repeated. The recess 52' has a conically-shaped portion. Thus, when the cable retaining insert 5' is tightened, the contact area between the head 42 and the cable retaining insert 5' is substantially that of a sphere and a cone which may be substantially a line contact. A conically-shaped recess 52' may be easier to manufacture compared to the spherically-shaped recess 52. The use of the cable retaining insert 5' is the same as described for the previous embodiment.

Figure 15:
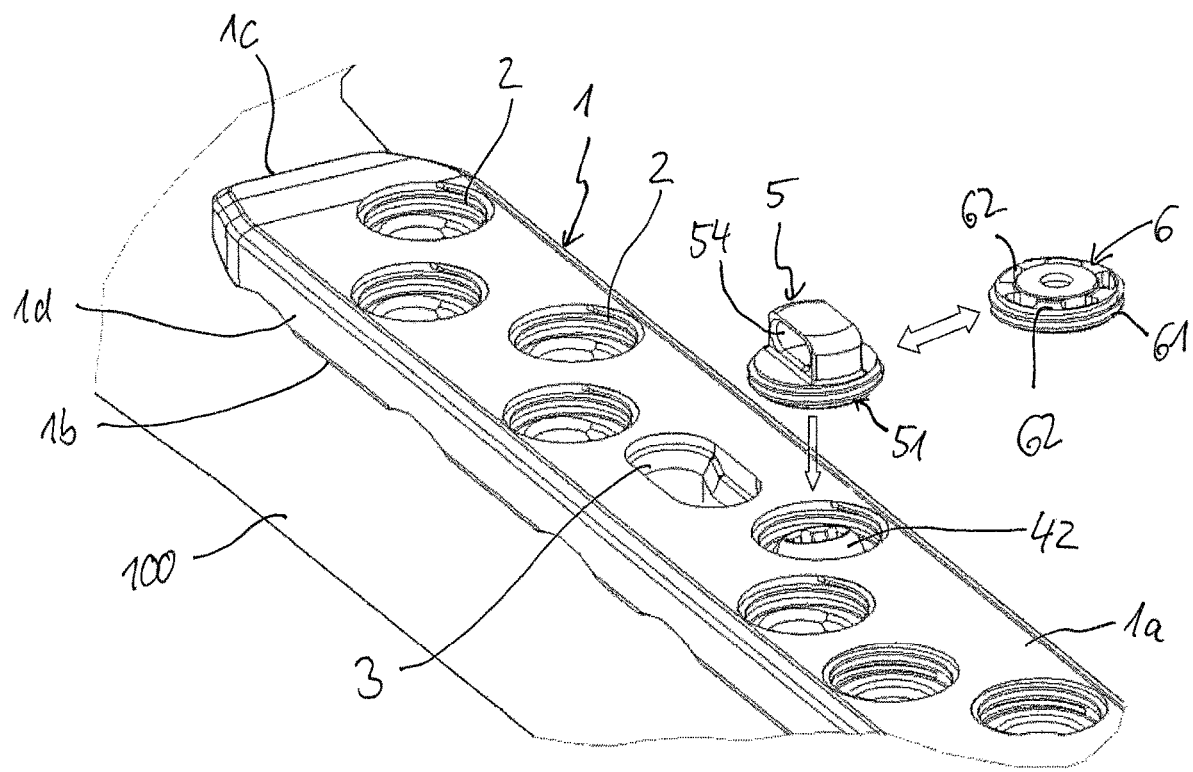
FIG. 15 shows a perspective view of a bone plate assembly with a cable retaining insert of the previous embodiments and a locking element usable interchangeably.

Referring now to FIG. 15, a further embodiment of the bone plate assembly additionally includes a locking member 6 that can be used interchangeably with the cable retaining insert 5 or the cable retaining insert 5'. The locking member 6 is a substantially cylindrical member with an external thread 61 that is configured to cooperate with the internal thread 23a of the cylindrical bore 23 of the hole 2. At the bottom side, a recess (not shown), for example a spherically-shaped recess or a conically-shaped recess similar to the recess 52 or 52' of the cable retaining insert 5, 5' is provided that may engage the head 42. At its upper side, the locking member 6 comprises one or more drive recesses 62 for engagement with a drive tool for inserting and tightening the locking member 6.

With the bone plate assembly including the locking member 6 the variety of applications can be further increased. For example, one hole 2 with a bone anchor 4 may be provided with the locking member 6 and another hole 2 with another bone anchor 4 may be provided with the cable retaining insert 5, 5'. Alternatively, after a specified time of healing of the fracture, the cable 200 and the cable retaining insert 5, 5' may be removed and replaced by a locking member 6.

Modifications of the above described embodiments may be contemplated. For example, the second portion 53 of the cable retaining insert may have more than one aperture. It may also be contemplated that the aperture is hook-like, i.e. not a closed loop. The shape of the second portion 53 may also be different. The first portion 51, 51' may have another engagement structure different from a thread to cooperate with a corresponding engagement structure of the hole. For example, a snap-in connection based on friction may also be contemplated. The first portion may also protrude above the top side 1a of the plate member.

The ramp consisting of the recess 21a may be omitted. The seat 21 for the head provided in the hole 2 may have another shape as long as it cooperates with the head in the manner of a ball-and-socket joint. The thread 51a is shown to be a single thread, however, can also be a double or a multiple thread. The threads may extend only along a portion of the first portion or the cylindrical bore, respectively.

The shape of the plate member 1 is not restricted to the embodiments shown. Other shapes are also conceivable. The bone anchor is not limited to a bone screw which has a threaded shank. Smooth, barbed or roughened pins are also conceivable. Further, any known bone anchors may be used.

The locking element may have any structure for engagement with a drive tool.

There have been described and illustrated herein several embodiments of a cable retaining insert, bone plate assemblies with cable retaining inserts, and method of using the same. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its scope as claimed.

What is claimed is:

1. A cable retaining insert configured to be used with a plate member of a bone plate assembly, the cable retaining insert including:
    a top side and an opposite bottom side,
    a first portion adjacent to the bottom side comprising an engagement structure configured to be directly retained by a corresponding engagement structure defined by the plate member,
    a second portion adjacent to the top side comprising at least one aperture configured to retain a cable to the plate member,
    wherein the first portion of the cable retaining insert has a spherically-shaped or conically-shaped recess at the bottom side for receiving at least a portion of a head of a bone anchor.

2. The cable retaining insert of claim 1, wherein the first portion comprises an external thread that is configured to cooperate with an internal thread of a hole in the plate member.

3. The cable retaining insert of claim 2, wherein the external thread is continuous about the first portion.

4. The cable retaining insert of claim 1, wherein the aperture has an elongate shape.

5. The cable retaining insert of claim 4, wherein the engagement structure defines a central axis of the cable retaining insert and wherein a long side of the aperture extends substantially perpendicular to the central axis.

6. The cable retaining insert of claim 1, wherein the engagement structure defines a central axis of the cable retaining insert and wherein a first width of the second portion in a first direction substantially perpendicular to the central axis is smaller than a second width in a second direction substantially perpendicular to the central axis, and wherein the second width does not exceed a width of the first portion in a direction perpendicular to the central axis.

7. The cable retaining insert of claim 1, wherein the aperture forms a closed loop.

8. The cable retaining insert of claim 1, wherein the first portion and the second portion are formed monolithically.

\* \* \* \* \*